US012582833B2

(12) United States Patent
Horinek et al.

(10) Patent No.: US 12,582,833 B2
(45) Date of Patent: Mar. 24, 2026

(54) WEARABLE FABRIC FOR PHOTO-STIMULATING A BIOLOGICAL SYSTEM

(71) Applicants: David Horinek, Weare, NH (US); Trenton Horinek, Weare, NH (US); Eric Tuscia, Cranston, RI (US)

(72) Inventors: David Horinek, Weare, NH (US); Trenton Horinek, Weare, NH (US); Eric Tuscia, Cranston, RI (US)

( * ) Notice: Subject to any disclaimer, the term of this patent is extended or adjusted under 35 U.S.C. 154(b) by 727 days.

(21) Appl. No.: 18/057,616

(22) Filed: Nov. 21, 2022

(65) Prior Publication Data

US 2023/0158326 A1      May 25, 2023

Related U.S. Application Data

(60) Provisional application No. 63/281,562, filed on Nov. 19, 2021.

(51) Int. Cl.
*A61N 5/06* (2006.01)
(52) U.S. Cl.
CPC ........... *A61N 5/062* (2013.01); *A61N 5/0616* (2013.01); *A61N 2005/063* (2013.01); *A61N 2005/0645* (2013.01); *A61N 2005/0661* (2013.01); *A61N 2005/0663* (2013.01)
(58) Field of Classification Search
USPC ........................................... 623/16.11–23.56
See application file for complete search history.

(56) References Cited

U.S. PATENT DOCUMENTS

| | | | |
|---|---|---|---|
| 2003/0009158 A1* | 1/2003 | Perricone | A61K 8/365 607/91 |
| 2015/0177423 A1* | 6/2015 | Scipioni | A41D 13/005 428/221 |
| 2017/0362744 A1* | 12/2017 | Piergallini | A61N 5/062 |

FOREIGN PATENT DOCUMENTS

EP            2388023 A1 * 11/2011   ........... A61K 38/085

* cited by examiner

*Primary Examiner* — Arti Singh-Pandey

(57) ABSTRACT

A wearable fabric for photo-stimulating a biological system includes at least one piece of textile, a plurality of bioceramic particles, and at least one nutrient-based precursor. The at least one piece of textile includes a plurality of interwoven polymeric fibers, an outer textile surface, and an inner textile surface. The outer textile surface and the inner textile surface are positioned opposite to each other about the at least one piece of textile. The quantity of bioceramic particles is uniformly integrated amongst the plurality of interwoven polymeric fibers. The at least one nutrient-based precursor is integrated amongst the plurality of interwoven polymeric fibers as the at least one nutrient-based precursor is configured to frictionally dislodge from the plurality of interwoven polymeric fibers as the inner textile surface is in physical contact with a wearer's skin to stimulate the production of Vitamin D and to stimulate bone growth.

14 Claims, 27 Drawing Sheets

WEARABLE FABRIC FOR PHOTO-STIMULATING A BIOLOGICAL SYSTEM

The current application claims a priority to the U.S. provisional patent application Ser. No. 63/281,562 filed on Nov. 19, 2021. The current application is filed on Nov. 21, 2022 while Nov. 19, 2022 was on a weekend.

FIELD OF THE INVENTION

The present invention relates generally to a textile material fiber with the ability to help increased production of Vitamin D and production of bone density. More specifically, the present invention is a wearable fabric that can replicate the effects of sunlight on the human body by utilizing bio-ceramic particles that dynamically respond with the human body's wavelength of 940 nanometers (nm) is peak emission with the body at rest.

BACKGROUND OF THE INVENTION

Depending on the part of the world an individual lives in, the lack of exposure to sunlight directly contributes to various health problems due to depriving the human body of a normal level of 'bio-nutrients' and 'rhythmic stimulation' that are essential for various mind-body functions such as regulating brain chemistry, essential hormones, and circadian rhythms. This mal illumination especially plays a role in the winter months where the natural production of Vitamin D within our bodies drops, causing issues such as Seasonal Affective Disorder (SAD) where peoples general mood drops. Throughout the years color and light have played a vital part in human health, survival, and culture, with white light playing an important role that is made up of many different colors, each with its own wavelength and vibrational frequency, many of which are not visible to the human eye. As technology has advanced over the years to the modern medicine that we know today, the healing properties of various colored light, such as blue being an effective treatment for various physical and psychological diseases, has taken a backseat. Vitamin D plays an important role in regulating the calcium and phosphorus levels within the body, ensuring proper functioning of the kidneys, intestines, and the stability of the skeletal system. Currently many individuals attempt to obtain their Vitamin D needs by exposing themselves to sunlight, eating foods containing Vitamin D and taking supplements with Vitamin D. For many individuals with changing seasons or indoor job requirements, getting the necessary exposure to the sun is not an easy task, resulting in Vitamin D deficiency. The recommended 10 to 30 minutes of midday sunlight, several times a week is not always possible for everyone, especially for those with more melanin, who require additional time out in the sun. Furthermore, due to various medications or increased risk to sunlight related diseases such as skin cancer or lupus, some individuals do not have the option to get daily exposure to sunlight. Additionally, Vitamin D can be acquired through various food groups such as fish, dairy and cereal products, and some fortified foods, however not all of these foods are available to everyone. Similar to Vitamin D supplements these foods cost more and are sometimes not accessible to individuals in food deserts.

An objective of the present invention is to provide users with a source of Vitamin D, that relies on the body's own heat to fluorescence and be absorbed and reflected safely back onto the body. The present invention also promotes mineral retention and growth in bone cells to increase bone density. The present invention intends to provide users with a device that utilizes its unique material to stimulate biological and chemical processes within humans, animals, or the environment. In order to accomplish that, a preferred method of the present invention comprises an element sourcing step, a mixing step, a yarn manufacturing step, a fabric manufacturing step, a final use preparation step, and a garment manufacturing step. Further, the element sourcing step ensures a unique combination of bio-ceramic particle blends selected to bioluminescent at a particular wavelength to stimulate the body's biological and chemical responses to naturally make its own Vitamin D. Thus, the present invention is a unique blend of finely ground bio-ceramic particles permanently embedded inside a synthetic yarn polymer matrix that are further made into garments and apparel to be worn close to the skin, to stimulate naturally occurring health benefits.

SUMMARY OF THE INVENTION

The present invention is a bio-photonic textile designed to improve photo-stimulation of biological systems and environments using films, yarns, knitted, woven materials, non-woven textiles, and clothing. The present invention seeks to develop and commercialize a textile yarn or range of yarns, knitted, woven and nonwoven materials to generate wavelengths of 280-380 nanometers (nm) in the ultraviolet (UV) spectrum that is able to increase Vitamin D production and bone density in humans and animals when worn next to the skin. In order to accomplish this the present invention comprises an element sourcing step that ensures the proper type and amount of both the masterbatch of bio-ceramic blends and the dry polymer matrix chips. Further, the mixing step ensures the masterbatch is properly ground up to complete the yarn extrusion process. Additionally, the yarn manufacturing step combines the sourced elements into a yarn of various cross-section types with various colors. Further, the fabric manufacturing step ensures the yarn is created into a fabric material with a variety of methods such as being knitting. Furthermore, the final use preparation step readies the fabric for garment manufacturing and may add additional coatings onto the fabric. Finally, the garment manufacturing step turns the fabric into a clothing item or apparel that can be closely worn next to the skin to provide various health benefits. Thus, the present invention is a unique blend of finely ground bio-ceramic particles permanently embedded inside a synthetic yarn polymer matrix that are further made into garments and apparel to be worn close to the skin, to stimulate naturally occurring health benefits.

DETAIL DESCRIPTIONS OF THE INVENTION

All illustrations of the drawings are for the purpose of describing selected versions of the present invention and are not intended to limit the scope of the present invention.

Figure 1:
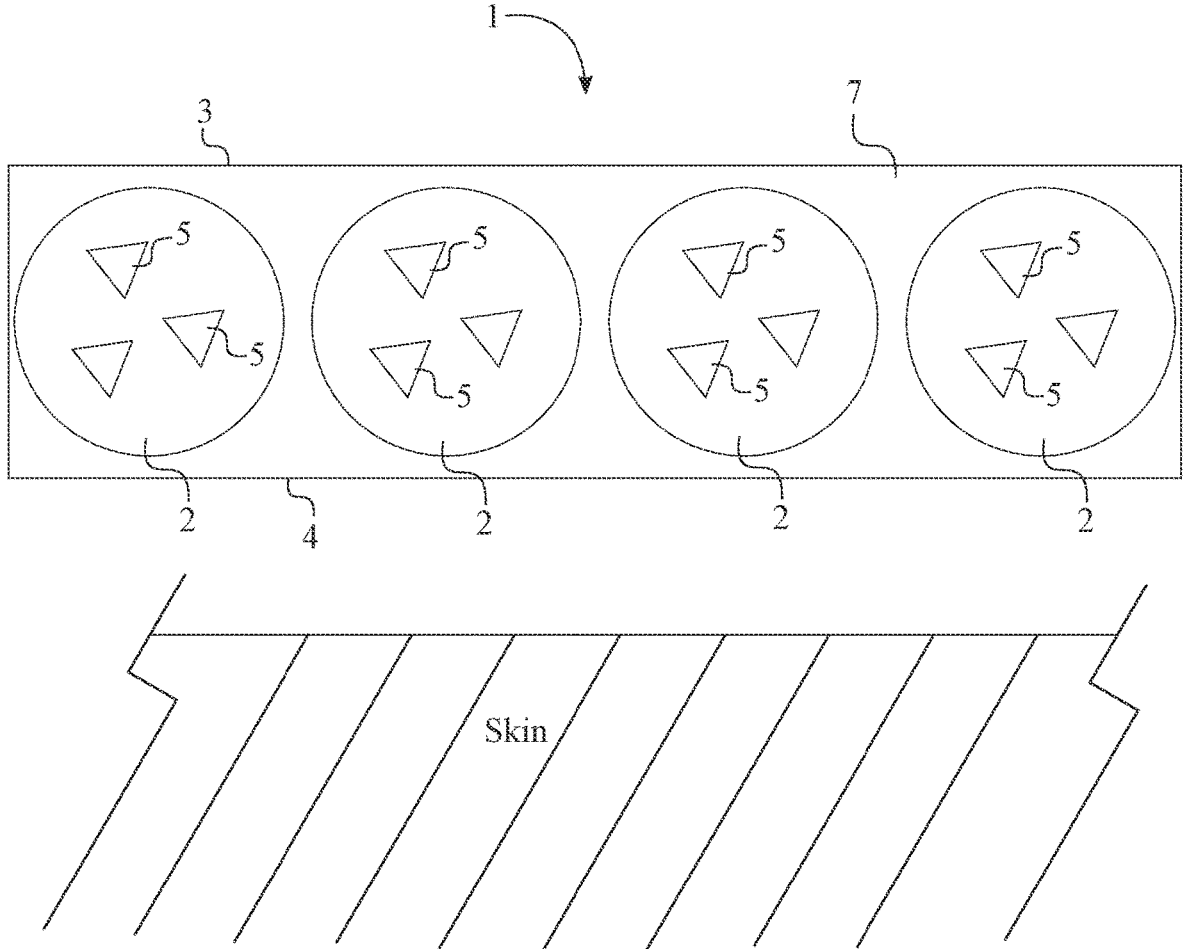
FIG. 1 is a schematic view of the present invention.
Figure 2:
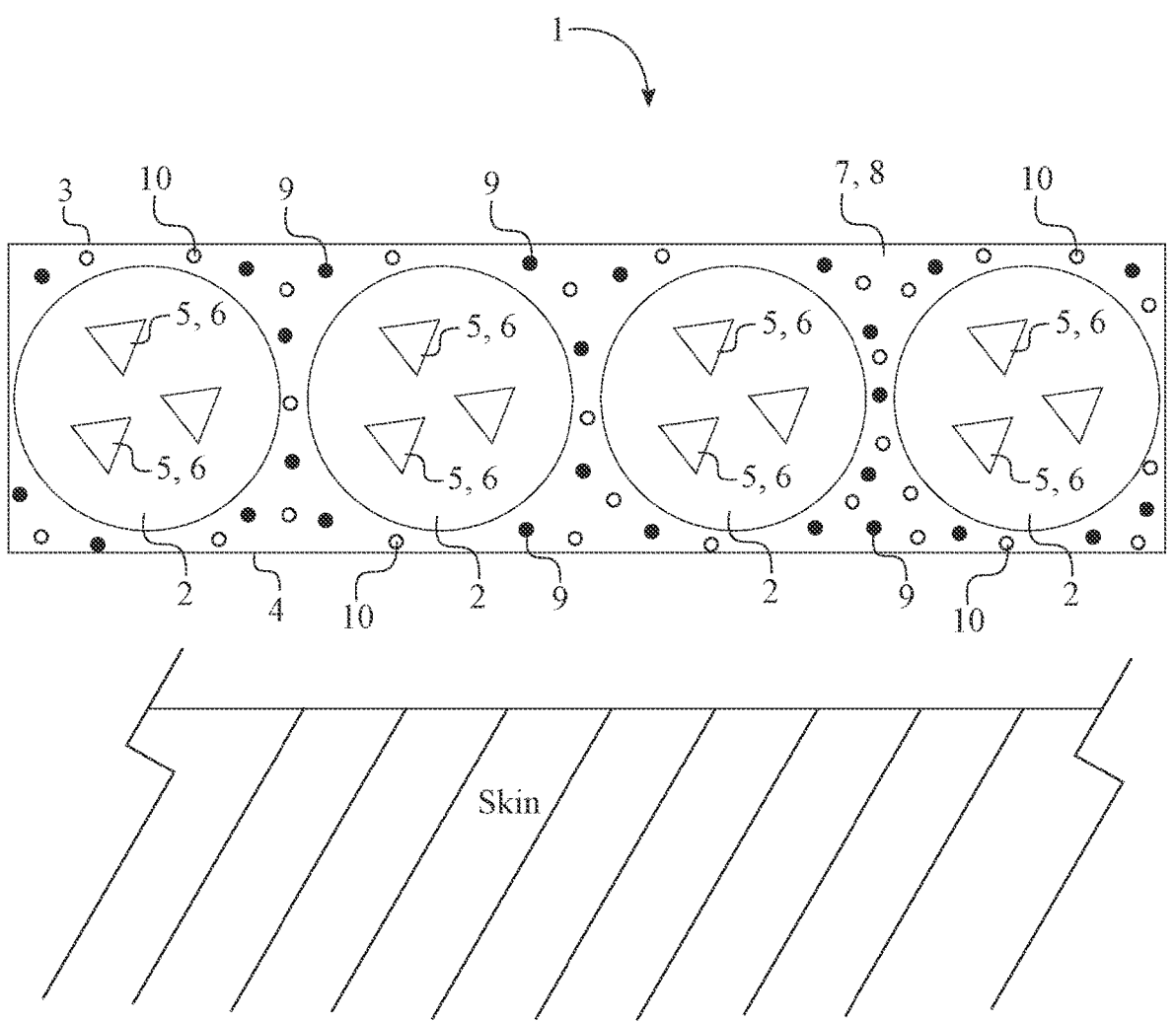
FIG. 2 is a schematic view of the present invention with the first nutrient-based precursor.
Figure 3:
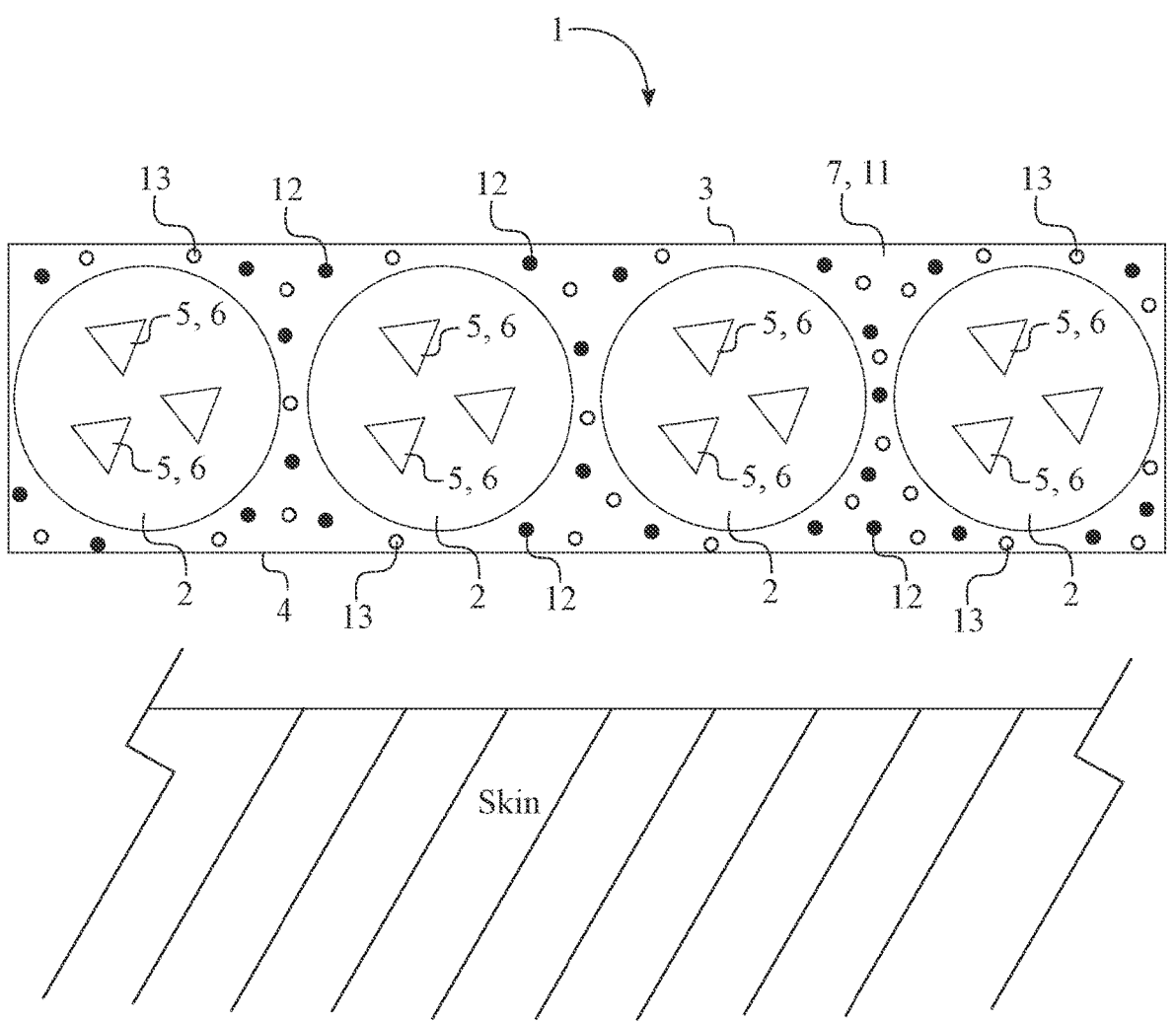
FIG. 3 is a schematic view of the present invention with the second nutrient-based precursor.
Figure 4:
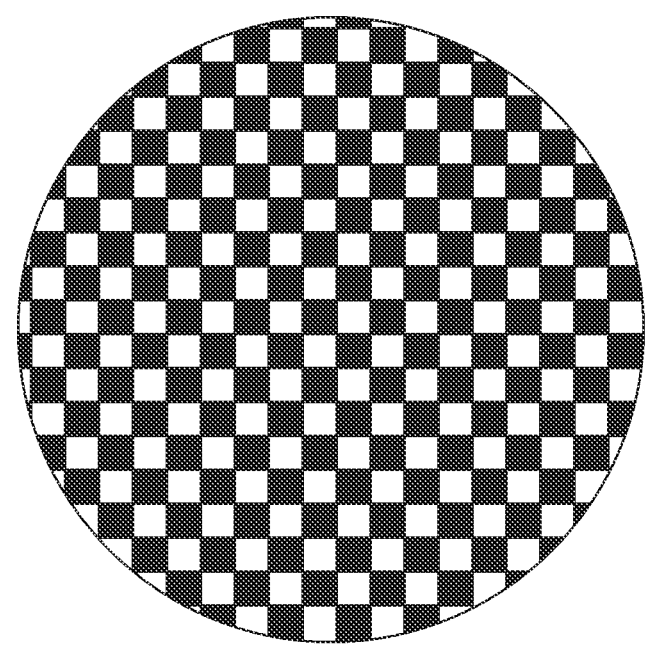
FIG. 4 is an illustration of a potential cross section of the present invention.

As shown in FIGS. 1-3, the present invention is a wearable fabric for photo-stimulating a biological system of the wearer when worn close to the skin. An objective of the present invention is to provide a unique natural alternative method of stimulating the human body's skin to create its own Vitamin D when exposure of direct sunlight is not possible and increase bone growth. The present invention intends to provide users with a device that can create a textile material or apparel to replicate the effects of sunlight on the human skin to naturally stimulate the production of Vitamin D within the body when worn next to the skin and to stimulate bone growth.

In reference to FIG. 1, the present invention comprises at least one piece of textile 1, a plurality of bioceramic particles 5, and at least one nutrient-based precursor 7 in order to accomplish the intended functionalities (stimulate the production of Vitamin D and bone growth). The at least one piece of textile 1 can be configured into at least one piece of clothing, at least one wearable patch, or any other kind of wearable fabric. The at least one piece of textile 1 comprises a plurality of interwoven polymeric fibers 2, an outer textile surface 3, and an inner textile surface 4. More specifically, the outer textile surface 3 and the inner textile surface 4 being positioned opposite to each other about the at least one piece of textile 1 so that the wearable fabric can be oriented in relation to a wearer's skin. In other words, the outer textile surface 3 is oriented away from the wearer and positioned offset from the wearer's skin. The inner textile surface 4 is positioned adjacent to the wearer and is in physical contact with the wearer's skin. The quantity of bioceramic particles that filters the sun's rays is uniformly integrated amongst the plurality of interwoven polymeric fibers 2. For example, the plurality of interwoven polymer fibers can be nylon, acrylic, viscose, hemp, or any other type of similar fibers. The at least one nutrient-based precursor 7 is integrated amongst the plurality of interwoven polymeric fibers 2 to stimulate Vitamin D production and/or stimulate bone growth. More specifically, the at least one nutrient-based precursor 7 is configured to frictionally dislodge from the plurality of interwoven polymeric fibers 2 as the inner textile surface 4 is in physical contact with the wearer's skin.

In reference to FIG. 2 and FIG. 3, the plurality of bioceramic particles 5 is preferably a plurality of violet glass particles 6. Each of the plurality of violet glass particles 6 is configured to filter electromagnetic radiation with a wavelength less than 295 nanometers (nm) and electromagnetic radiation with a wavelength greater than 380 nm. In order to accomplish the filtration of electromagnetic particles, a particle diameter size for each of the plurality of violet glass particles 6 is formed between 0.2 nm to 5 micrometers ($\mu$m). Preferably, the plurality of violet glass particles 6 is embedded or coated with the plurality of interwoven polymer fibers and considered as the energy source within the present invention. More specifically, the plurality of bioceramic particles 5 acts as a natural barrier thus blocking out harmful sunlight and allowing beneficial inferred light and ultraviolet light to pass through. As a result, the plurality of bioceramic particles 5 is able to activate the at least one nutrient-based precursor 7.

In reference to FIG. 2, the at least one nutrient-based precursor 7 that is broken down with the friction and absorbed into the wearer's skin to stimulate the production of Vitamin D may comprise a first nutrient-based precursor 8. More specifically, the first nutrient-based precursor 8 comprises a quantity of dehydrocholesterol 9 and a quantity of first absorption catalyst 10, wherein the quantity of dehydrocholesterol 9 and the quantity of first absorption catalyst 10 are homogenously mixed with each other into a first coating solution. The quantity of dehydrocholesterol 9 functions as a cholesterol precursor and is photochemically converted to Vitamin $D_3$ in the wearer's skin, therefore functioning as provitamin-$D_3$. The presence of the quantity of dehydrocholesterol 9 in human skin enables humans to manufacture Vitamin $D_3$ (cholecalciferol) from ultraviolet UV-B rays in the sun light, via provitamin-$D_3$, an intermediate isomer. The quantity of first absorption catalyst 10 is a 2% solution of Fulvic acid. Furthermore, the first nutrient-based precursor 8 is configured to topically administer between 0.05 milligrams (mg) to 1 mg of the first coating solution into the wearer's skin.

In reference to FIG. 3, the at least one nutrient-based precursor 7 that is broken down with the friction and absorbed into the wearer's skin to stimulate the production of bone growth may comprise a second nutrient-based precursor 11. More specifically, the second nutrient-based precursor 11 comprises a quantity of *Cissus quadrangularis* 12 and a quantity of second absorption catalyst 13, wherein the quantity of *Cissus quadrangularis* 12 and the quantity of second absorption catalyst 13 are homogenously mixed with each other into a second coating solution. The quantity of *Cissus quadrangularis* 12 increases insulin-like growth factors (IGF) signaling in bone cells, which promotes mineral retention and growth. The quantity of *Cissus quadrangularis* 12 promotes bone growth, mineral density, and increases the bone's ability to withstand force. The quantity of second absorption catalyst 13 is a 2% solution of Fulvic acid. Furthermore, the second nutrient-based precursor 11 is configured to topically administer between 1 mg to 10 mg of the second coating solution into the wearer's skin.

Figure 12:
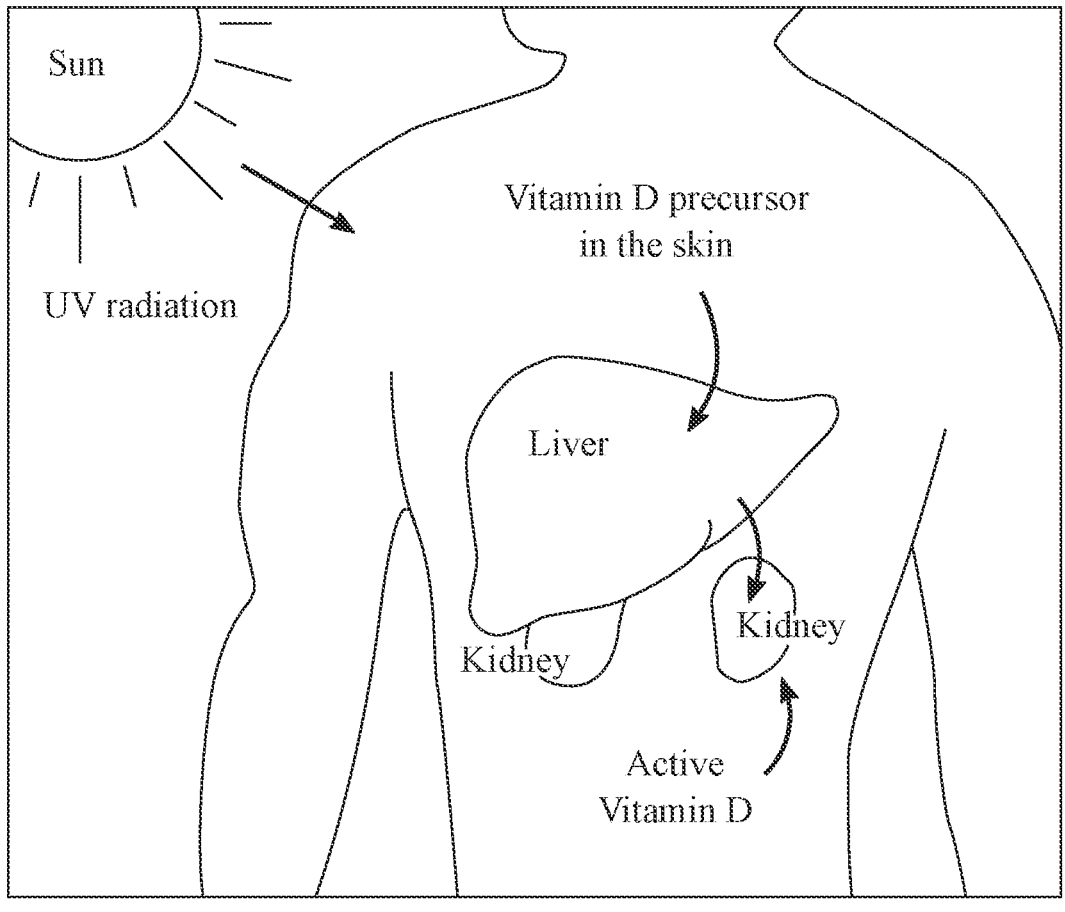
FIG. 12 is an illustration of how a human body produces Vitamin D from sunlight.

In reference to FIG. 12, the at least one piece of textile 1, the plurality of bioceramic particles 5, and the at least one nutrient-based precursor 7 are configured to generate Vitamin D within and promote bone growth to a wearer's body as the at least one nutrient-based precursor 7 is frictionally released from the plurality of interwoven polymeric fibers 2 and is absorbed into the wearer's body and as electromagnetic radiation is attenuated to a specific ultraviolet range by the plurality of bioceramic particles 5 and is absorbed into the wearer's body. In order to optimize utilization of the present invention, the specific ultraviolet range is a wavelength between 285 nm and 380 nm.

In order to initiate the manufacture process, the plurality of bioceramic particles 5 is sourced and wet milled into smaller particles that range between 0.2 nm to 5 μm. Then, the plurality of bioceramic particles 5 is integrated into a polymer of choice that can be, but is not limited to Polyethylene Terephthalate, Nylon, Acrylic, Viscose, and Hemp. Once the plurality of bioceramic particles 5 and the polymer of choice are integrated into each other, a polymer chip is formed with a concentration of 1-30% of the plurality of bioceramic particles 5. The polymer chip is then extruded into a filament yarn or a staple fiber with a particle load between 0.2-5% by utilizing known extrusion technologies. The filament or staple fiber with the plurality of bioceramic particles 5 is then knitted into the plurality of interwoven polymeric fibers 2 so that the at least one textile can be created. The at least one textile is then constructed into a garment to be worn next to the wearer's skin. The plurality of bioceramic particles 5 that is embedded or coated with the garment is considered the energy source of the present invention. The garment is then micro encapsulated and applied with the at least one nutrient-based precursor 7 by utilizing known spray system or known bath system, wherein the at least one nutrient-based precursor 7 can be the quantity of dehydrocholesterol 9, the quantity of *Cissus quadrangularis* 12 or both the quantity of dehydrocholesterol 9 and the quantity of *Cissus quadrangularis* 12.
Supplemental Description In reference to FIGS. 13-26, the present invention comprises an element sourcing step, a mixing step, a yearn manufacturing step, a fabric manufacturing step, a final use preparation step, and a garment manufacturing step. Many of these components allow for the user function to receive their necessary Vitamin D levels to maintain healthy bodily functions. Each of the steps of the present invention operate in sequential order starting with the element sourcing step and ending with the garment manufacturing step. Within a few steps there are various methodology options to complete the textile production. Thus, the present invention is a unique blend of finely ground bioceramic particles permanently embedded inside a synthetic yarn polymer matrix that are further made into garments and apparel to be worn close to the skin, to stimulate naturally occurring health benefits.

Figure 5:
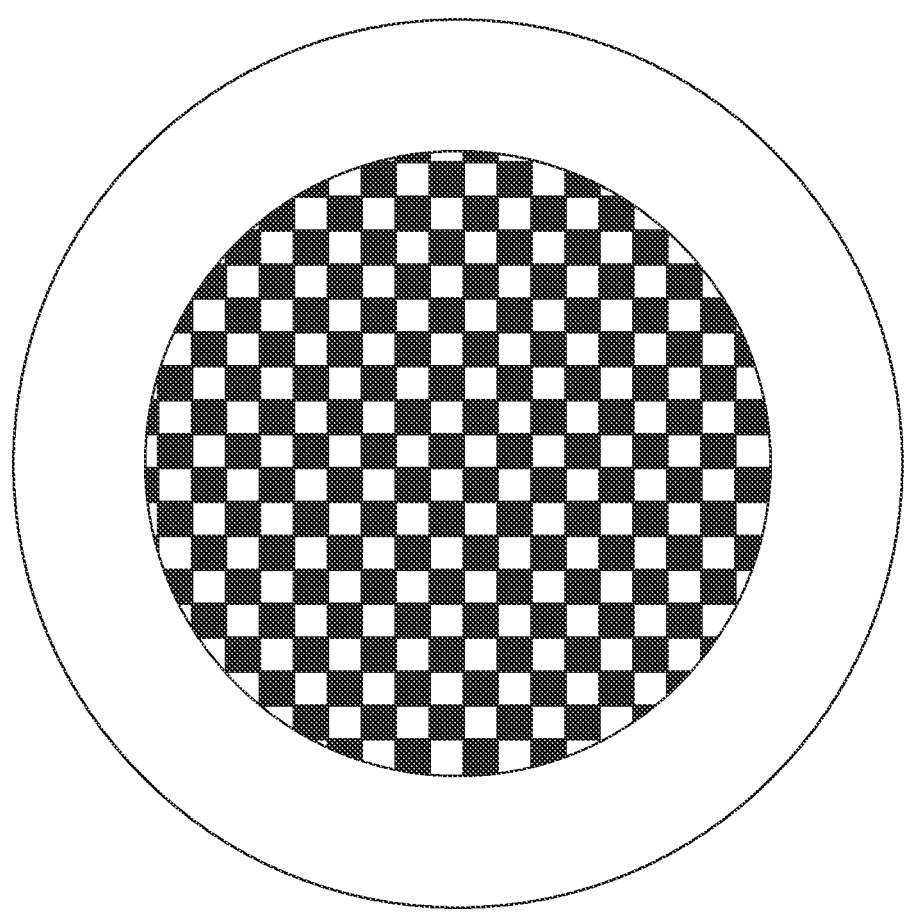
FIG. 5 is an illustration of a potential cross section of the present invention.
Figure 6:
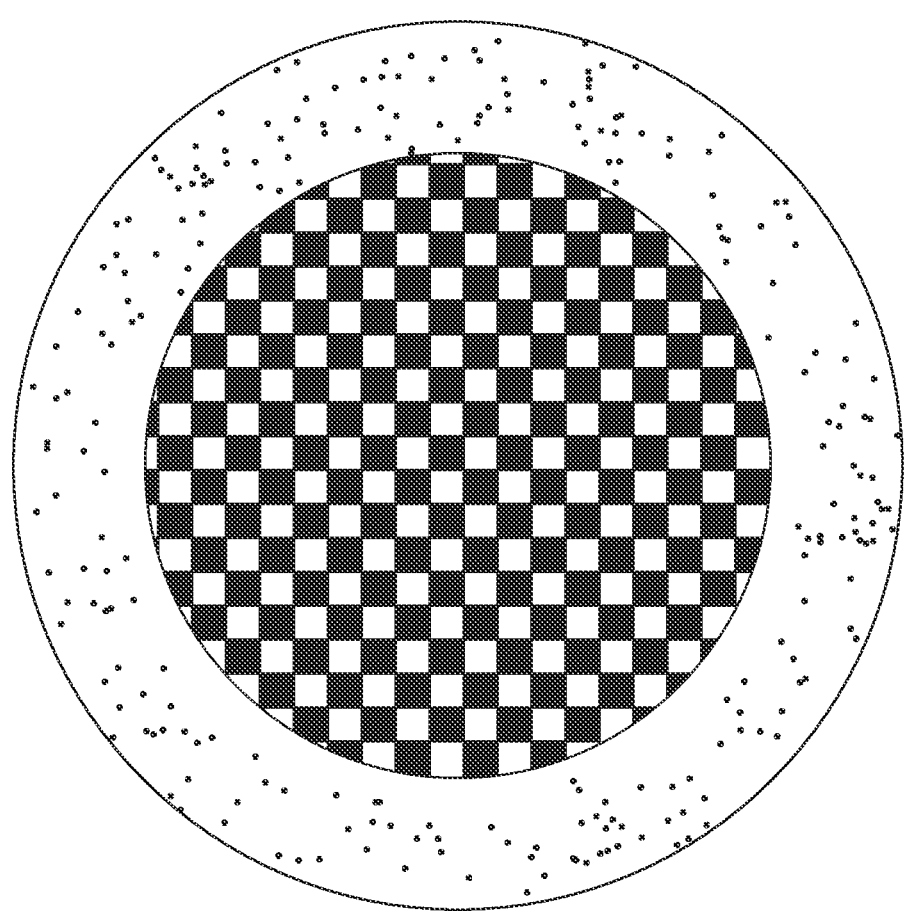
FIG. 6 is an illustration of a potential cross section of the present invention.
Figure 7:
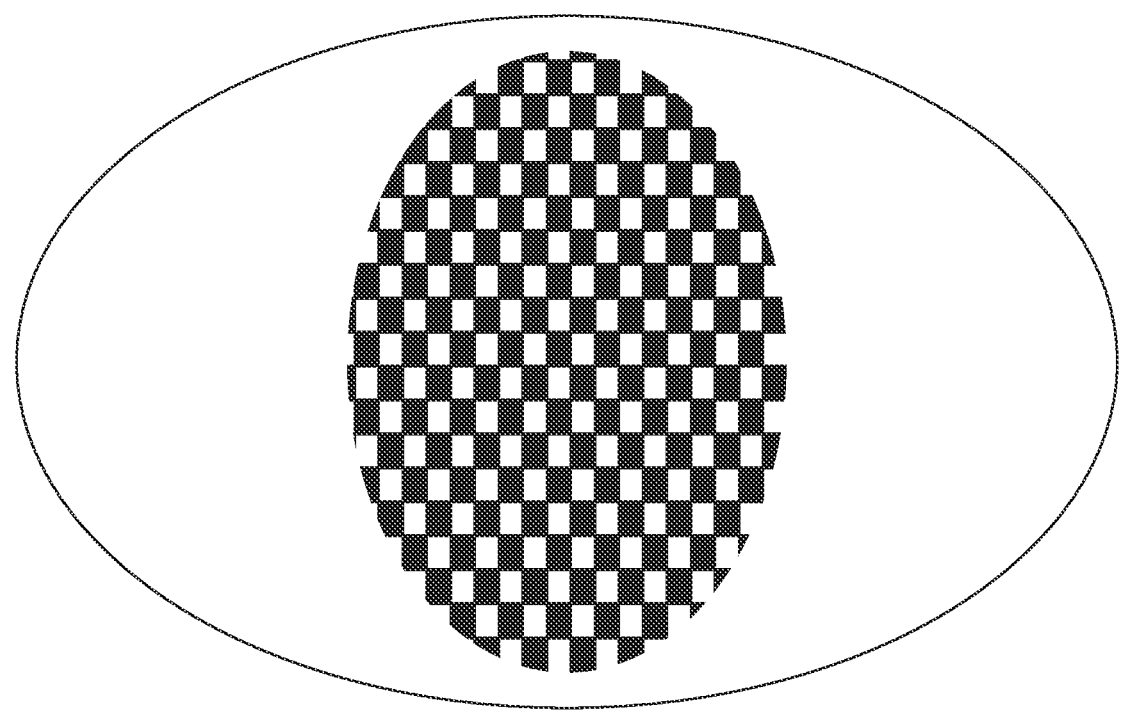
FIG. 7 is an illustration of a potential cross section of the present invention.
Figure 8:
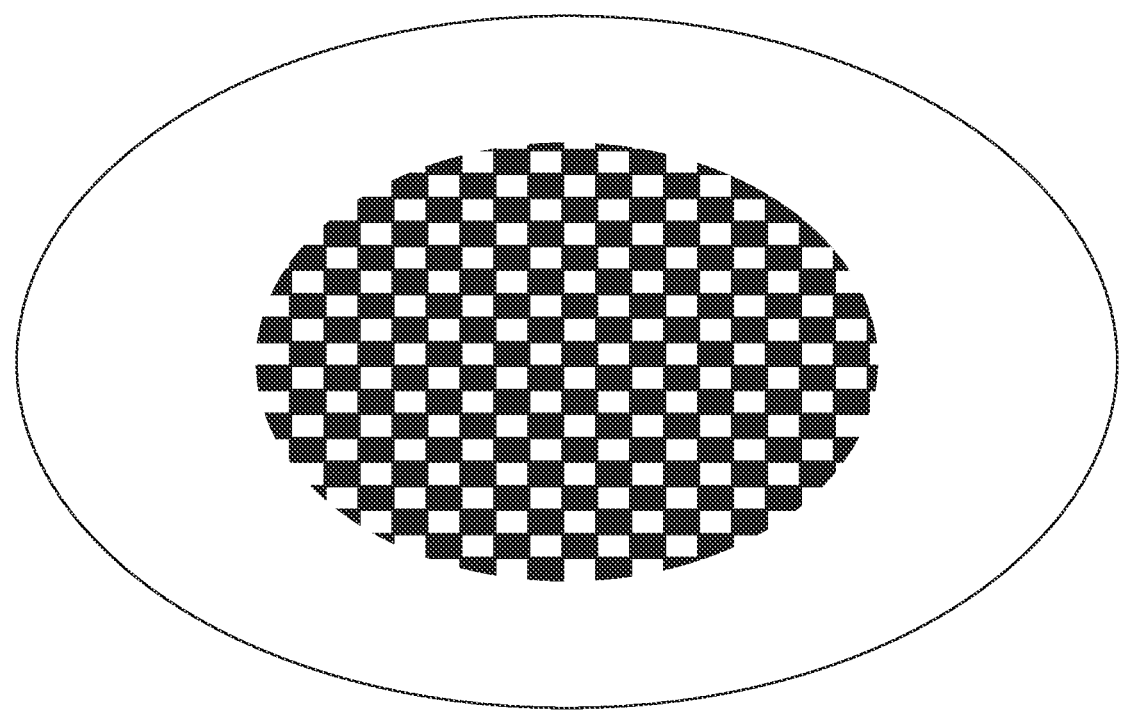
FIG. 8 is an illustration of a potential cross section of the present invention.
Figure 9:
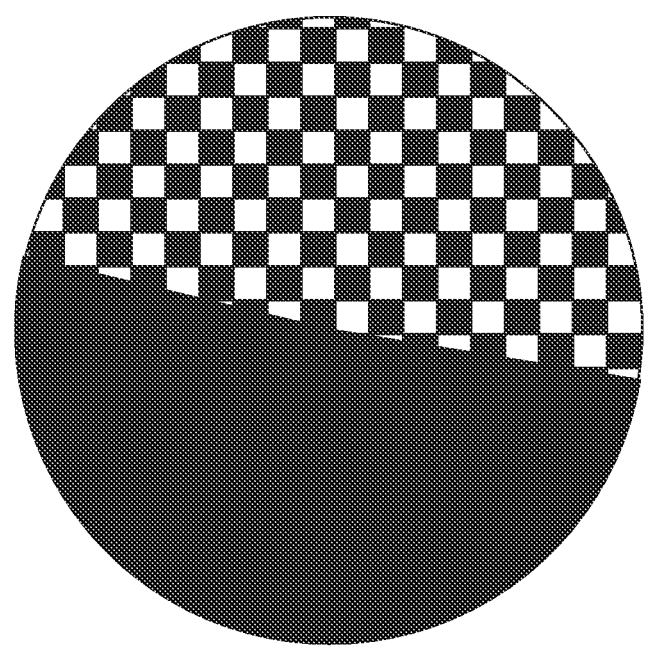
FIG. 9 is an illustration of a potential cross section of the present invention.
Figure 10:
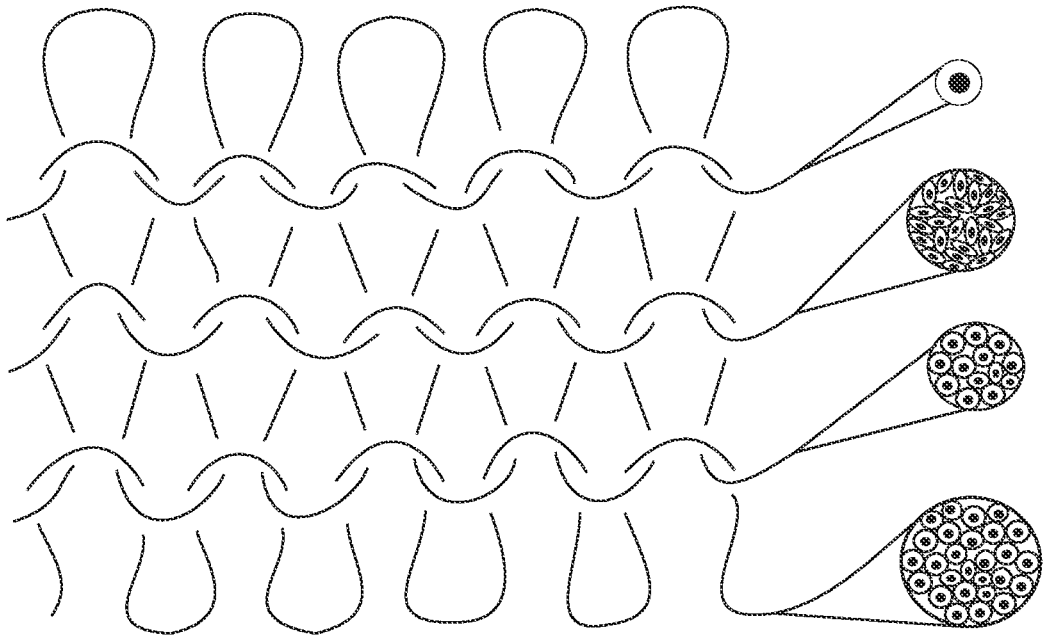
FIG. 10 is an illustration of a knit fabric construction view of the present invention.

The present invention is a fiber with the ability to help increase production of Vitamin D. In its preferred embodiment the Vitamin D stimulating textile comprises a bioceramic particle blend, a dry polymer matrix chips, and a coating. The bioceramic particle blend is designed with finely ground particles that can be permanently embedded inside a synthetic multifilament yarn as shown in FIG. 5. The first bioceramic particle blend is selected to bioluminescent at a particular wavelength. Further the bioceramic particles are combined in a unique blend of metals, materials, and rare earth to create a masterbatch. Furthermore, the bioceramic particle blend of minerals and other nano particles are saturated with infrared energy that re-emit back to the skin tissue to stimulate Nitric Oxide production, increasing muscle recovery and to increase Vitamin D production. The bioceramic particle blend is designed with a 1-to-5-micron size that is mixed with color additives and dry polymer matrix chips. The dry polymer matrix chips preferably use a polyester polymer due to its polarization properties but is not limited to only this polymer. The dry polymer matrix chips combine with the bio-ceramic particle blend to create a variety of potential material cross sections as shown in FIGS. 4-9. The resulting mixture can then have a coating applied that is designed to be excited by long-wave, ultraviolet light and to fluoresce at specific wavelengths. The coating enhances the wearer's comfort, health benefits and efficacy. The coating comprises a plurality of encapsulations of micro beads that adhere to the surface of the present invention and rupture while being worn to release the select nutrients to nurture the skin, enhancing and accelerating the natural Vitamin D process as shown in FIG. 12. It should be further noted that, the Vitamin D stimulating textile can be created in many various shapes, sizes, and methods and the yarn cross section can have several variations while still staying within the scope of the present invention.

Figure 13:
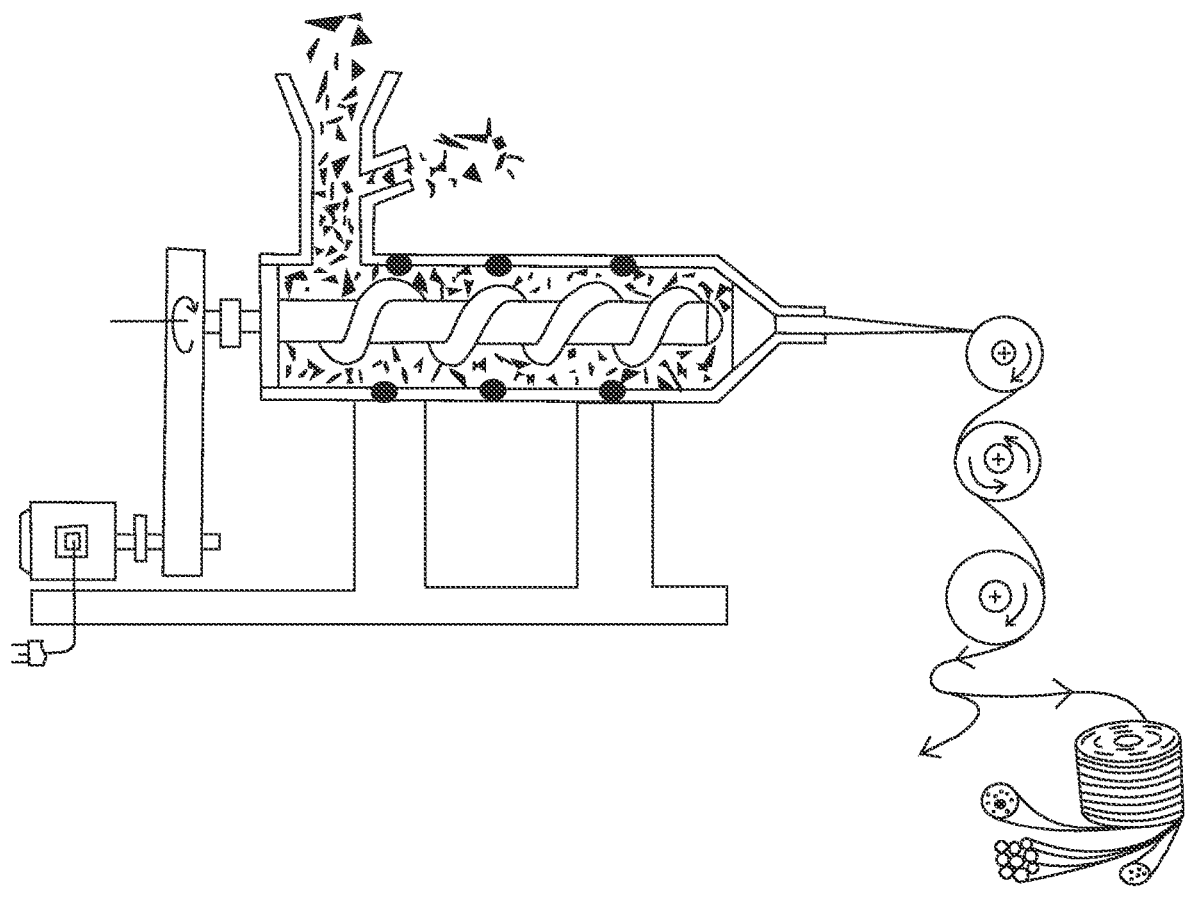
FIG. 13 is an illustration of the melt spinning synthetic yarn extrusion process.
Figure 14:
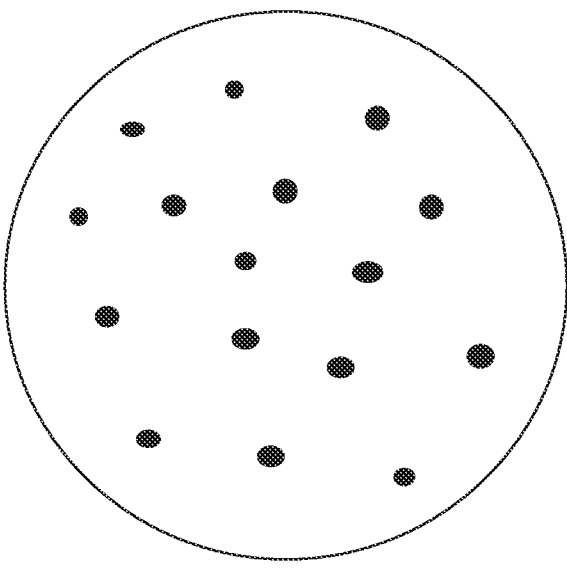
FIG. 14 is an illustration of a potential filament cross section of the present invention.
Figure 15:
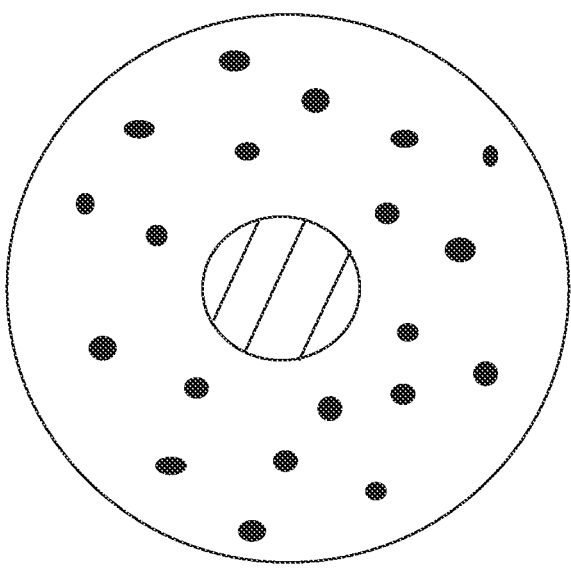
FIG. 15 is an illustration of a potential filament cross section of the present invention.
Figure 16:
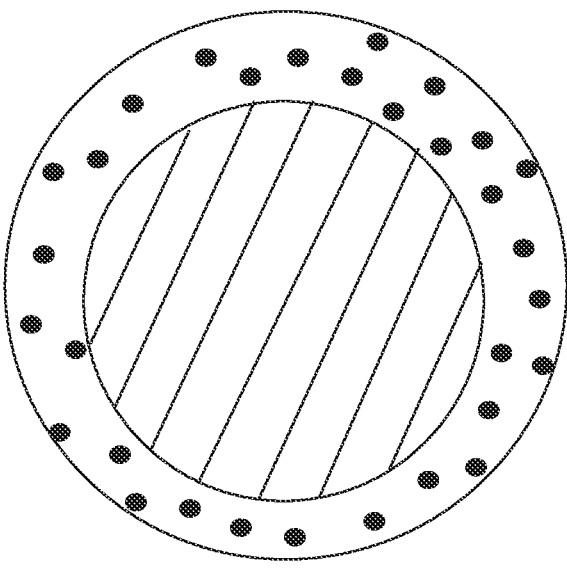
FIG. 16 is an illustration of a potential filament cross section of the present invention.
Figure 17:
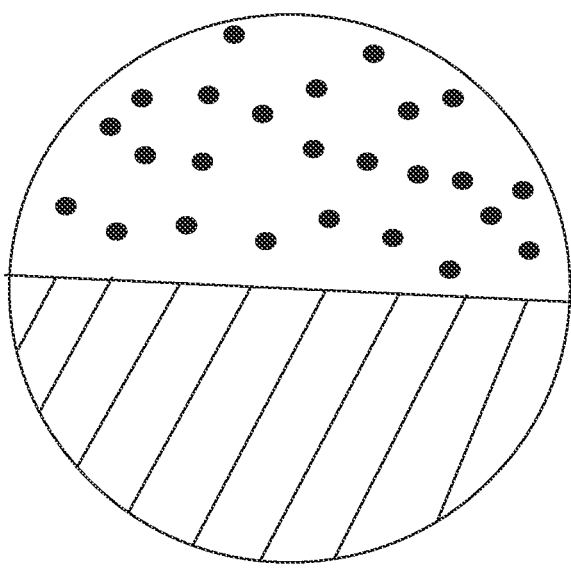
FIG. 17 is an illustration of a potential filament cross section of the present invention.
Figure 18:
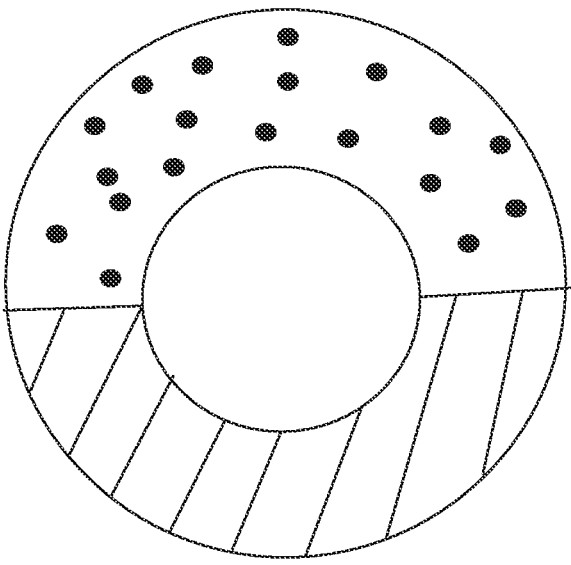
FIG. 18 is an illustration of a potential filament cross section of the present invention.
Figure 19:
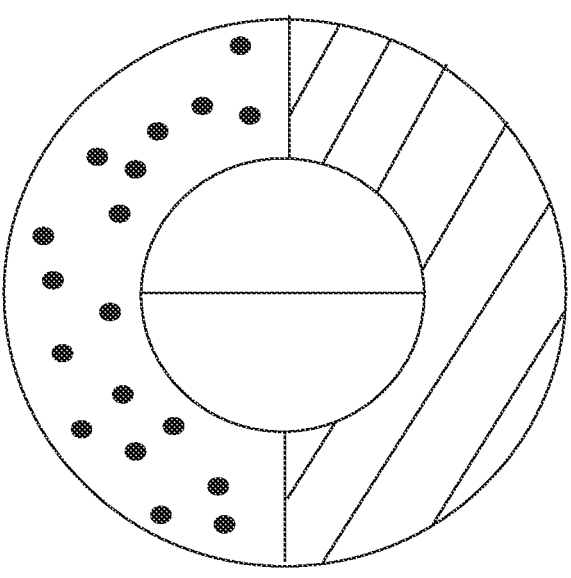
FIG. 19 is an illustration of a potential filament cross section of the present invention.
Figure 20:
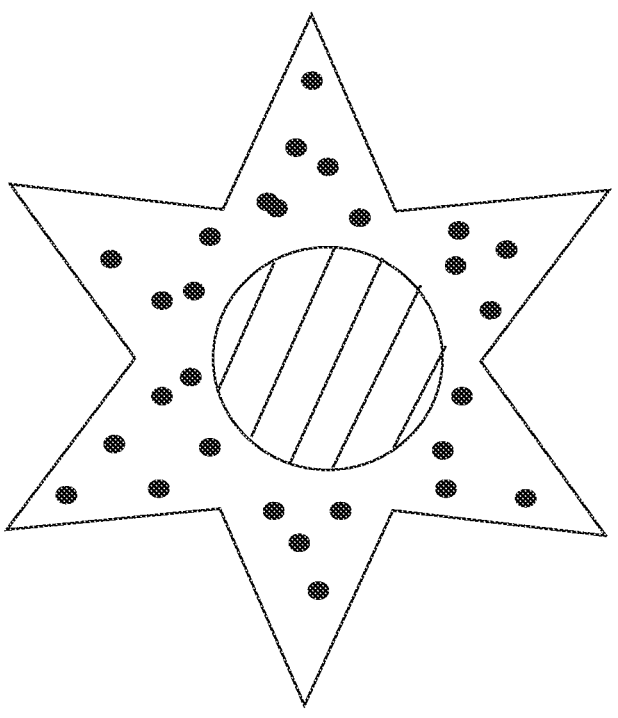
FIG. 20 is an illustration of a potential filament cross section of the present invention.
Figure 21:
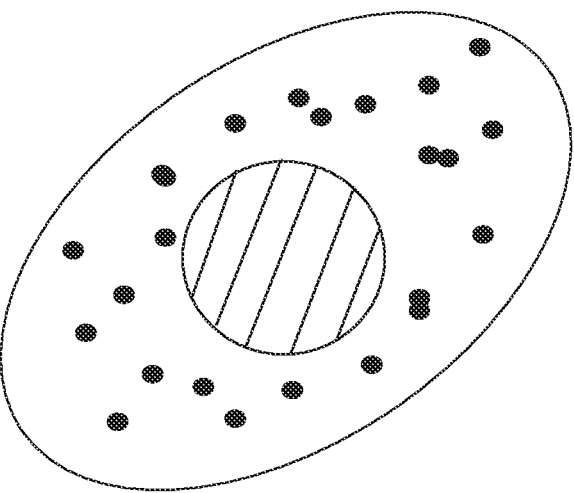
FIG. 21 is an illustration of a potential filament cross section of the present invention.
Figure 22:
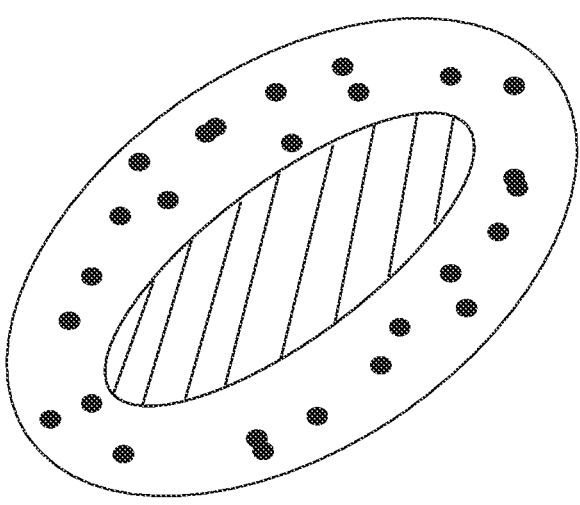
FIG. 22 is an illustration of a potential filament cross section of the present invention.

The Vitamin D stimulating textile method of production starts with the element sourcing step. In its preferred embodiment the element sourcing step comprises an element type selection, a measuring step, an element property selection, and a matrix chip selection. The element type selection can utilize a range of specifically selected bioceramic elements to be combined with a blend of metals, minerals, and rare earth. The bioceramic element types, amount and combination can be sourced world-wide allowing the element property selection to include bioluminescent amounts ranging from 0.1% to 6% that are up to 30% the weight of the yarn. The matrix chip selection preferably utilizes a polyester polymer but can utilize an assortment of commercial polymers such as nylon, polypropylene, polyethylene and other regenerated cellulose fibers. Further all the components are measured out to ensure the masterbatch is introduced to the polymer matrix chips during the yarn filament extrusion process to create a 1% to 10% concentration of yarn by composition as seen in FIG. 13.

Figure 23:
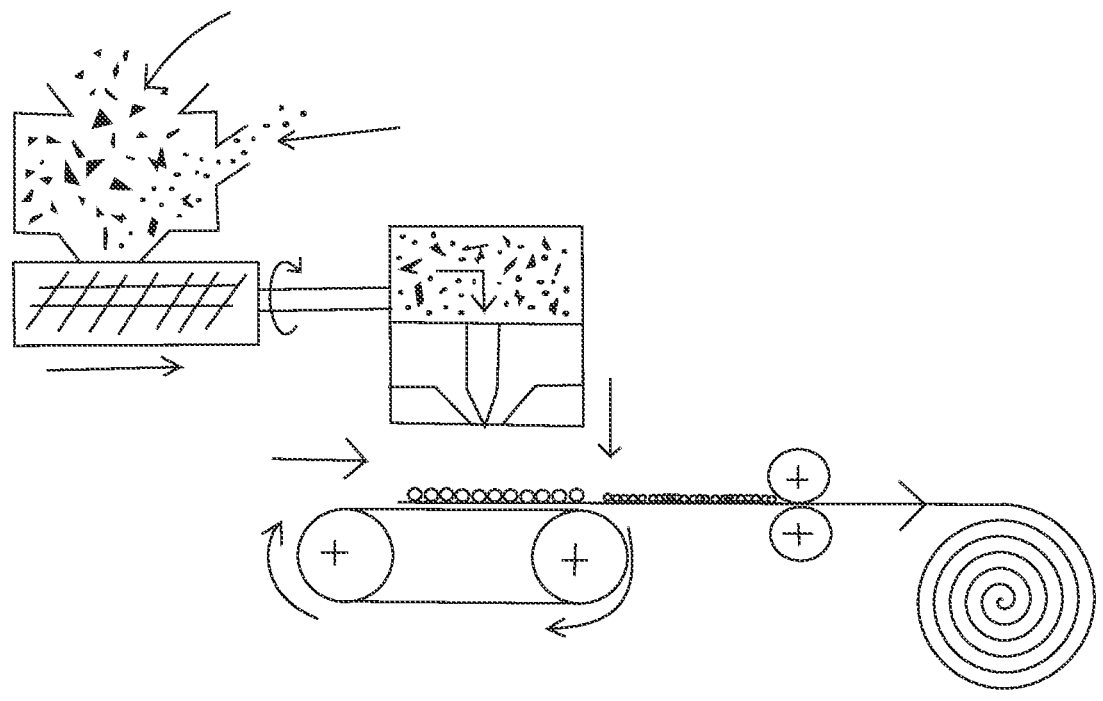
FIG. 23 is an illustration of the melt extrusion synthetic non-woven process.

After the element sourcing step, the mixing step occurs. In its preferred embodiment the mixing step comprises a two main parts. To prepare the bioceramic particle blend, that is combined with various other elements to form a masterbatch, for the yarn manufacturing step the masterbatch needs to enter a workable size and state. The masterbatch is finely ground up to the size of 1-5 microns to allow for embedding. This ground-up masterbatch can include unique performance additives such as UV inhibitors, wicking, antimicrobial, and other performance characteristics. This design allows for the ground bioceramic nano particles to be fine enough so as not to block the holes in the filament fiber extrusion head. As shown in FIG. 23, once the masterbatch is ground up, the masterbatch is intimately mixed together with the dry polymer matrix chips in order to start the yarn manufacturing step.

Figure 27:
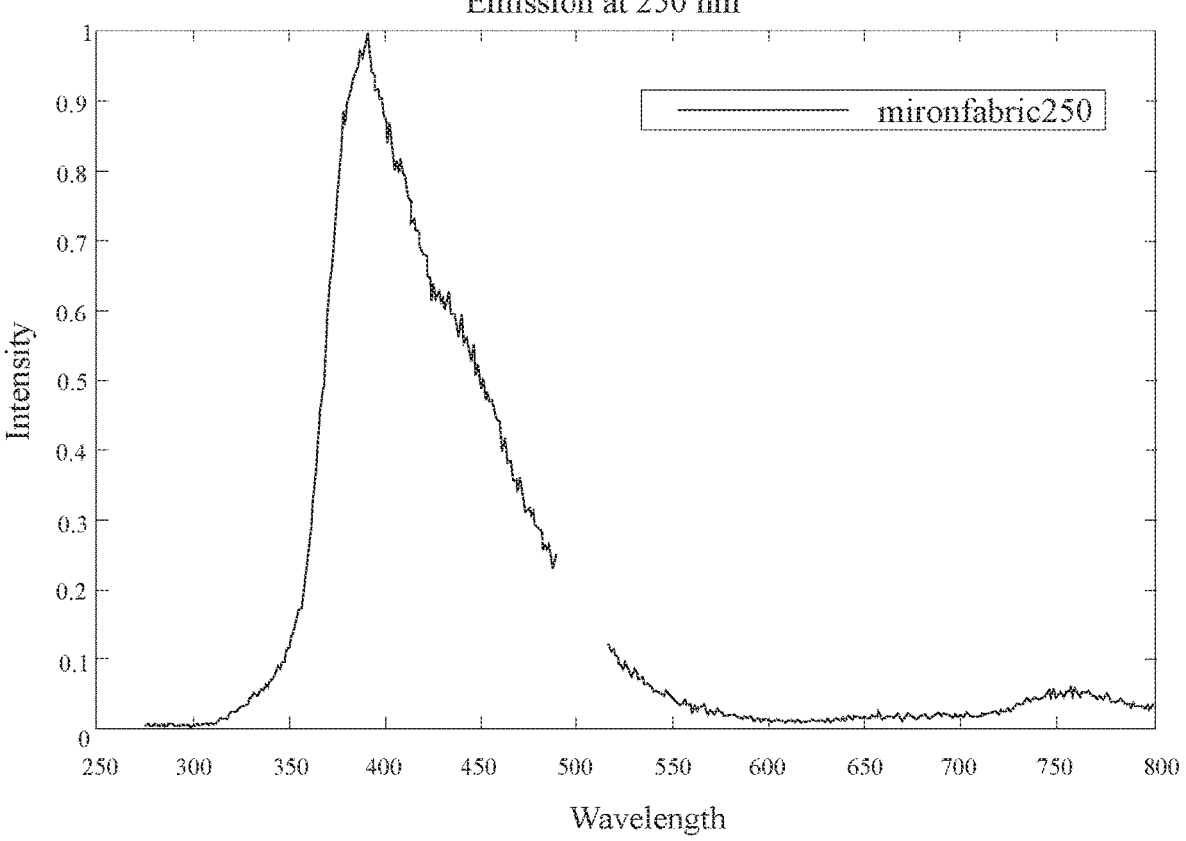
FIG. 27 is an illustration of a Texas University Lab Test report measuring emitted wavelengths using Fluorolog3 Fluorimeter.

The yarn manufacturing step starts after the masterbatch, and polymer matrix chips are properly mixed together within the mixing step. In its preferred embodiment the yarn manufacturing step comprises a melt extrusion spinning process, a yarn coloring, a property detail addition, and a cross section creation. The yarn manufacturing step mainly consists of the melt extrusion process. The melt extrusion process creates a synthetic yarn by melting the mixed materials, drying the resulting material, and melt spinning extrusion methods to create doped chips with bioceramic concentrate for further processing into melt blown non-woven and yarn suitable for clothing and apparel as shown in FIG. 27. As the mixed material goes though the heating and melting, the material is being spun within the mixer and extrusion chamber. At this point, the mixture can have added pigments to change the color of the yarn as well as additional materials to change various properties amount the end yarn result. The mixture is then pushed through a spin pack and metering pump to ensure the proper proportions go through the spinneret and are quenched with cold air, warm air, or a chemical bath. As the synthetic yarn leaves the spinneret, the cross section of the yarn can be designed in various ways as shown in FIGS. 14-22. This design allows for various filament cross section options. One cross section option is a round mono filament polymer matrix with 1% to 10% proprietary bioceramic particles dispersed throughout. Another cross-section option is a round bi-component extrusion formation with polymer matrix outer layer with 0.1% to 6% bioceramic blend B and a core of 0.1% to 6% bioceramic blend A. The third option is a round bi-component extrusion formation with a polymer matrix outer layer with 0.1% to 6% bioceramic blend B and a core of bioceramic blend A. Another option is an oval bi-component extrusion yarn formation with various core orientations. The final option is a round bi-component side by side extrusion formation. These various cross sections provide more reflective effects as the cross section moves towards an oval shape. Furthermore, the various cross sections provide an array of possibilities and health solutions.

Figure 11:
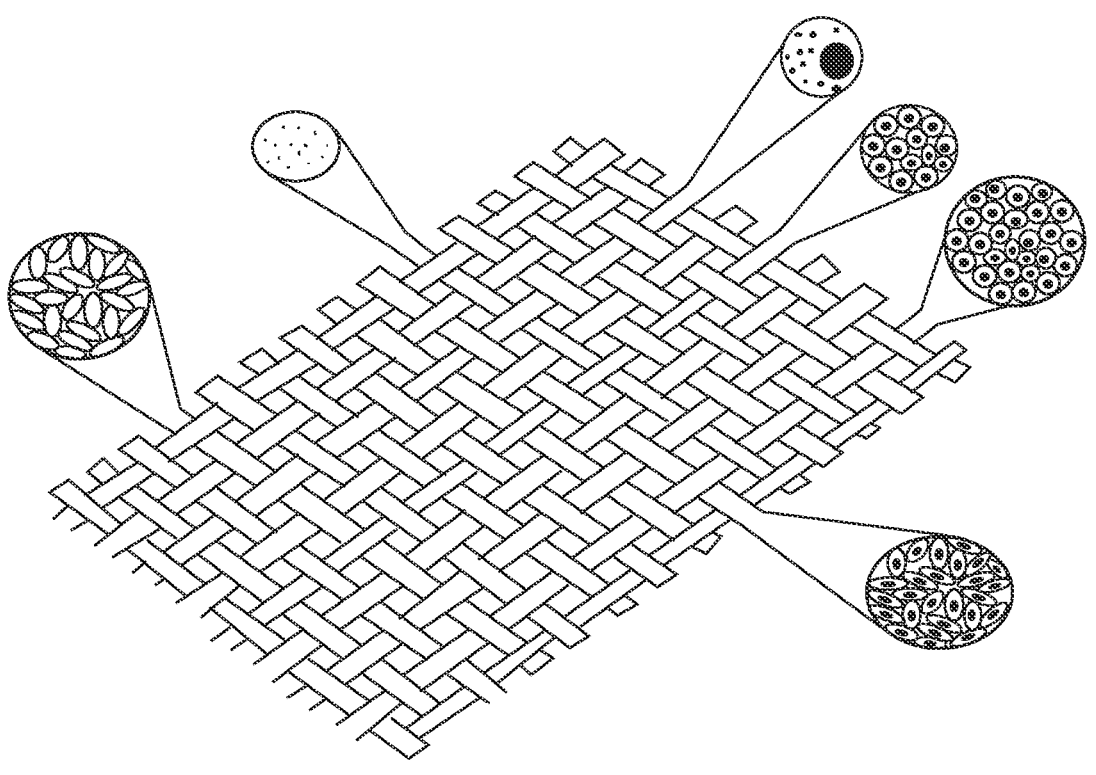
FIG. 11 is an illustration of a woven fabric view of the present invention.

The fabric manufacturing step begins once the yarn manufacturing step is complete. In its preferred embodiment, the fabric manufacturing step comprises three potential methods of manufacture; woven, knitted, or non-woven melt spun. The present invention can be manufactured using equipment that is commercially available worldwide. The synthetic yarn can be manufactured on most equipment for knitting such as a warp or weft. As seen in FIG. 11, the present invention can be woven or non-woven melt spun to create a fabric material. Furthermore, the synthetic yarn can be blended with other synthetic yarns and natural fibers during the fabric manufacturing step to create materials for textile apparel clothing and other applications for humans and animals.

Figure 24:
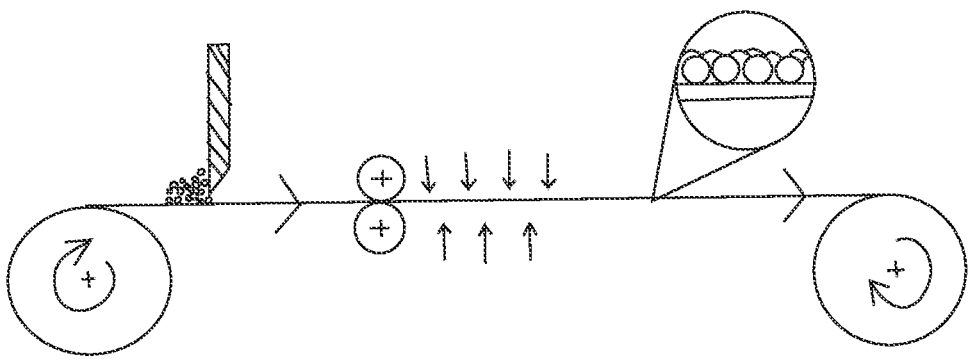
FIG. 24 is an illustration of the coating method on one side of the present invention.

The final use preparation step is then started after the fabric manufacturing step where the fabric is dyed and finished. In its preferred embodiment, the final use preparation step dyes and finished the fabric using conventional equipment that is commonly used in materials and apparel equipment commercially available worldwide. Conventional high pressure and temperature synthetic polymer dying equipment that is commonly used in the textile industry allows the fabric material to be colored a desired color using a solution. Furthermore, the fabric material goes through an optional coating process as shown in FIG. 24.

Figure 25:
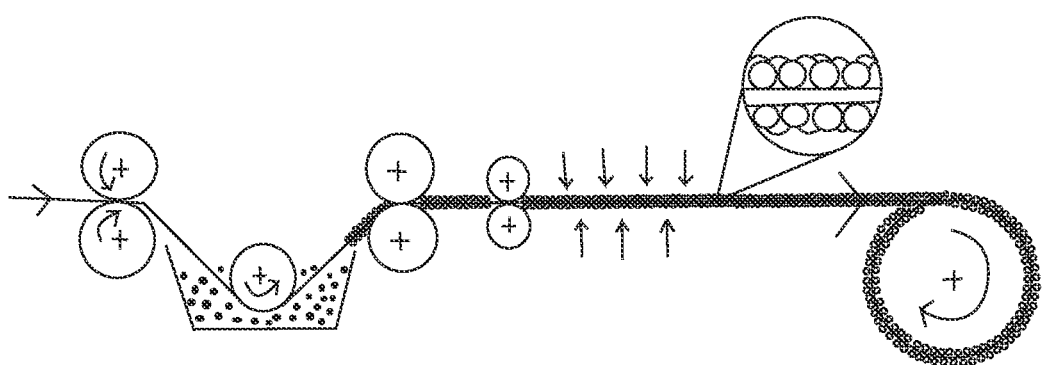
FIG. 25 is an illustration of the coating method on both sides of the present invention.
Figure 26:
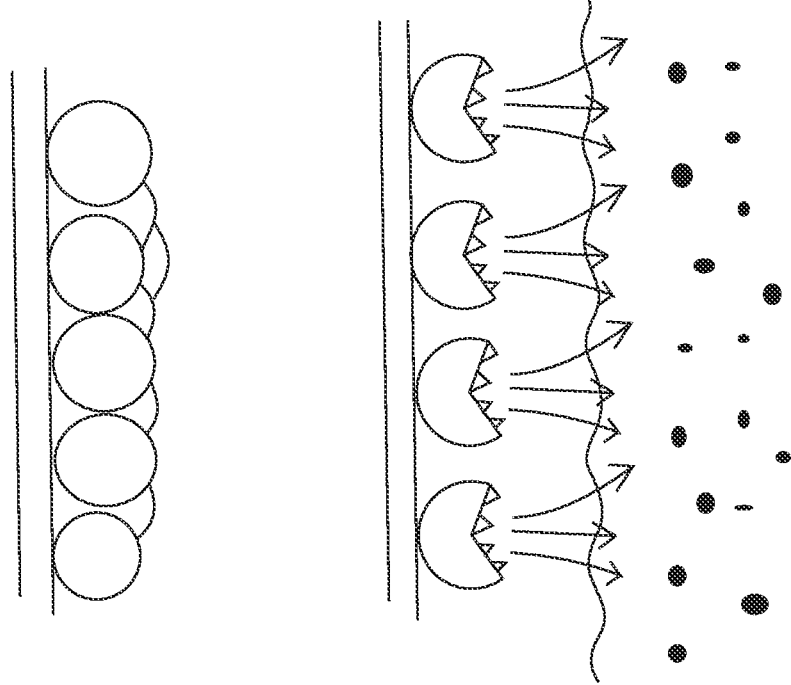
FIG. 26 is an illustration of the coating encapsulations and ruptured encapsulations.

The coating process places a special finished to one or both sides of the fabric which is the encapsulation of micro beads containing amino acids to accelerate, add nutrients and nurture the Vitamin D process within the body. As seen in FIG. 26, the coating of encapsulated beads adhere to the fabric substrate and rupture due to abrasion once being worn next to the skin, allowing the nutrients to flow onto the skin for additional health benefits. The fabric can be additionally laminated with two or more layers on either side as seen in FIG. 25, to add performance or comfort enhancing characteristics such as waterproofness, breathability, stretch, amongst various others. Finally, once the final use preparation step is complete, the fabric can then be used within the garment manufacturing step. The garment manufacturing step turns the fabric into any garment to be used by humans or animals. These garments can range from a variety of types such as wellness, sportwear, medical, workwear, aerospace, automotive, and casual wear ensuring inclusion for all types of clothing and apparel. With all the steps working with each other it can be seen that the present invention is a unique blend of finely ground bioceramic particles permanently embedded inside a synthetic yarn polymer matrix that are further made into garments and apparel to be worn close to the skin, to stimulate naturally occurring health benefits.

Although the invention has been explained in relation to its preferred embodiment, it is to be understood that many other possible modifications and variations can be made without departing from the spirit and scope of the invention as hereinafter claimed.

What is claimed is:

1. A wearable fabric for photo-stimulating a biological system comprising:
   at least one piece of textile;
   a plurality of bioceramic particles;
   at least one nutrient-based precursor;
   the at least one piece of textile comprising a plurality of interwoven polymeric fibers, an outer textile surface, and an inner textile surface;
   the outer textile surface and the inner textile surface being positioned opposite to each other about the at least one piece of textile;
   the plurality of bioceramic particles being uniformly integrated amongst the plurality of interwoven polymeric fibers;
   the at least one nutrient-based precursor being integrated amongst the plurality of interwoven polymeric fibers; and
   the at least one nutrient-based precursor being configured to frictionally dislodge from the plurality of interwoven polymeric fibers as the inner textile surface is in physical contact with a wearer's skin.

2. The wearable fabric for photo-stimulating a biological system as claimed in claim 1, wherein the plurality of bioceramic particles is a plurality of violet glass particles.

3. The wearable fabric for photo-stimulating a biological system as claimed in claim 2, wherein each of the plurality of violet glass particles is configured to filter electromagnetic radiation with a wavelength less than 295 nanometers (nm) and electromagnetic radiation with a wavelength greater than 380 nm.

4. The wearable fabric for photo-stimulating a biological system as claimed in claim 2, wherein a particle diameter size for each of the plurality of violet glass particles is between 0.2 nm to 5 micrometers (μm).

5. The wearable fabric for photo-stimulating a biological system as claimed in claim 1 comprising:

the at least one nutrient-based precursor comprising a first nutrient-based precursor;

the first nutrient-based precursor comprising a quantity of dehydrocholesterol and a quantity of first absorption catalyst; and the quantity of dehydrocholesterol and the quantity of first absorption catalyst being homogenously mixed with each other into a first coating solution.

6. The wearable fabric for photo-stimulating a biological system as claimed in claim 5, wherein the first nutrient-based precursor is configured to topically administer between 0.05 milligrams (mg) to 1 mg of the first coating solution into the wearer's skin.

7. The wearable fabric for photo-stimulating a biological system as claimed in claim 5, wherein the quantity of first absorption catalyst is a 2% solution of Fulvic acid.

8. The wearable fabric for photo-stimulating a biological system as claimed in claim 1 comprising:

the at least one nutrient-based precursor comprises a second nutrient-based precursor;

the second nutrient-based precursor comprises a quantity of *Cissus quadrangularis* and a quantity of second absorption catalyst; and the quantity of *Cissus quadrangularis* and the quantity of second absorption catalyst being homogenously mixed with each other into a second coating solution.

9. The wearable fabric for photo-stimulating a biological system as claimed in claim 8, wherein the second nutrient-based precursor is configured to topically administer between 1 mg to 10 mg of the second coating solution into the wearer's skin.

10. The wearable fabric for photo-stimulating a biological system as claimed in claim 8, wherein the quantity of second absorption catalyst is a 2% solution of Fulvic acid.

11. The wearable fabric for photo-stimulating a biological system as claimed in claim 1, wherein the at least one piece of textile, the plurality of bioceramic particles, and the at least one nutrient-based precursor are configured to generate Vitamin D within a wearer's body as the at least one nutrient-based precursor is frictionally released from the plurality of interwoven polymeric fibers and is absorbed into the wearer's body and as electromagnetic radiation is attenuated to a specific ultraviolet range by the plurality of bioceramic particles and is absorbed into the wearer's body.

12. The wearable fabric for photo-stimulating a biological system as claimed in claim 1, wherein the specific ultraviolet range is a wavelength between 285 nm and 380 nm.

13. The wearable fabric for photo-stimulating a biological system as claimed in claim 1, wherein the at least one piece of textile is configured into at least one piece of clothing.

14. The wearable fabric for photo-stimulating a biological system as claimed in claim 1, wherein the at least one piece of textile is configured into at least one wearable patch.

* * * * *